United States Patent [19]

Rauhut et al.

[11] 4,226,738

[45] Oct. 7, 1980

[54] N,N-BIS(TRIFLUOROMETHYLSULFONYL)OXAMIDES AND CHEMILUMINESCENT COMPOSITIONS CONTAINING THE SAME

[75] Inventors: Michael M. Rauhut, Bridgewater; Shin-Shyong Tseng, Raritan; Arthur G. Mohan, Somerville, all of N.J.

[73] Assignee: American Cyanamid Company, Stamford, Conn.

[21] Appl. No.: 956,567

[22] Filed: Nov. 1, 1978

[51] Int. Cl.$^2$ .................................................. C09K 3/00
[52] U.S. Cl. ........................ 252/188.3 CL; 260/556 S; 260/453 R; 260/465 D; 546/255; 560/13; 560/125; 560/150
[58] Field of Search .............. 260/556 S, 453, 465 D; 546/255; 560/13, 125, 150; 252/188.3 CL

[56] References Cited

U.S. PATENT DOCUMENTS

| | | | |
|---|---|---|---|
| 3,843,549 | 10/1974 | Bollyky | 252/188.3 CL |
| 4,005,141 | 1/1977 | Moore | 260/556 S |
| 4,022,828 | 5/1977 | Arnold et al. | 260/556 S |
| 4,053,430 | 10/1977 | Mohan | 252/188.3 CL |

*Primary Examiner*—Benjamin R. Padgett
*Assistant Examiner*—J. L. Barr
*Attorney, Agent, or Firm*—Gordon L. Hart

[57] ABSTRACT

N,N'-bis(trifluoromethylsulfonyl)oxamides are described with a number of variations by substitution at the amido nitrogen atoms. These compounds when used in chemiluminescent formulations will furnish superior light intensity and quantum efficiency. Preparation of compounds and their use for chemiluminescence are described.

19 Claims, No Drawings

N,N-BIS(TRIFLUOROMETHYLSULFONYL)OXAMIDES AND CHEMILUMINESCENT COMPOSITIONS CONTAINING THE SAME

The present invention relates to novel N,N'-bis(trifluoromethylsulfonyl)oxamide compounds, superior compositions containing said compounds which are useful for generating chemiluminescence by reaction with a hydroperoxide, and a process for generating chemiluminescence by reacting said superior compositions thereby.

The art has shown (Rauhut et al., U.S. Pat. No. 3,442,815, and Maulding, U.S. Pat. No. 3,400,080) that oxamides when reacted under particular conditions provide chemiluminescence. While the oxamides disclosed hitherto provide substantially high light intensity, the efficiency of the systems, as measured by the chemiluminescence quantum yield, is one percent, or lower.

There is a need, therefore, for compositions that will furnish superior light intensities over a long period of time and have a chemiluminescence quantum efficiency greater than one percent.

SUMMARY OF THE INVENTION

In accordance with the present invention, there are provided novel compounds represented by formula (I)

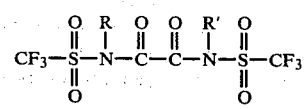

wherein R and R' independently represent hydrogen; alkyl of 1 to 6 carbon atoms; cycloalkyl of 4 to 8 carbon atoms; substituted alkyl or cycloalkyl wherein the substituents are selected from halo, carboxy, alkoxy, or alkoxycarbonyl, wherein the alkoxy is of 1 to 6 carbon atoms; alkanoyl of 2 to 18 carbon atoms; aroyl of 7 to 11 carbon atoms; aralkyl of 7 to 11 carbon atoms; carbocyclic aryl of 6 to 10 carbon atoms; heterocyclic aryl of 3 to 9 carbon atoms; substituted carbocyclic and heterocyclic aryl of 6 to 10 and 3 to 9 carbon atoms, respectively, wherein the substituents, one or more, are selected from halo, nitro, cyano, trifluoromethyl, alkyl and alkoxy of 1 to 6 carbon atoms, hydroxy, phenoxy, benzyloxy, phenyl, alkanoylamino 2 to 6 carbon atoms, benzoylamino, alkylsulfonyl of 1 to 6 carbon atoms, carboxy, alkoxycarbonyl and alkoxysulfonyl wherein the alkoxy group has 1 to 6 carbon atoms, $-SO_3^{\ominus}M^{\oplus}$ wherein $M^{\oplus}$ is a cation selected from sodium, potassium, lithium, ammonium, monoalkylammonium, dialkylammonium, trialkylammonium, or tetraalkylammonium wherein the alkyl radicals have 1 to 6 carbon atoms, and may be the same or different, aminocarbonyl, and aminosulfonyl which are unsubstituted or substituted at the nitrogen by 1 or 2 radicals selected from alkyl of 1 to 6 carbon atoms, phenyl, or substituted phenyl, wherein the substituents are as defined above for carbocyclic and heterocyclic aryl.

In accordance with the present invention, there are also provided compositions for reaction with a peroxide component to generate chemiluminescence comprising (a) a compound of formula (I), as previously defined, (b) an organic fluorescer compound, and (c) a diluent, said ingredients being present in proportions and concentrations sufficient to produce chemiluminescence when reacted with said peroxide component.

In accordance with the present invention, there is also provided a process for generating chemiluminescence comprising reacting the composition described hereinabove with a peroxide component.

Chemiluminescent compositions of the novel compounds of formula (I) find a wide variety of applications in emergency lighting devices (see U.S. Pat. No. 3,800,132) for the home, on the road, in coal mines, on lifevests, and on aircraft escape slides.

The compounds of the present invention can be used to provide long lasting chemiluminescence. They are particularly distinguished from the oxamides of U.S. Pat. Nos. 3,400,080 and 3,442,815 in that they provide superior chemiluminescence quantum yields, about 10-35%, versus about 1%, or lower, for the prior art oxamides.

DESCRIPTION OF PREFERRED EMBODIMENTS

The compounds of the present invention are readily prepared by reacting about two molecular proportions of the appropriate trifluoromethanesulfonamide, or trifluoromethanesulfonanilide, with oxalyl chloride in the presence of an acid binding agent by methods well-known in the art.

Methods for the preparation of the trifluoromethanesulfonanilides and N-substituted trifluoromethanesulfonamides are known in the art (see Harrington et al., U.S. Pat. Nos. 3,558,698; 3,629,332; 3,799,968; 3,865,844; 3,897,449; 3,920,444; and Moore et al., U.S. Pat. No. 3,609,187).

Examples of the compounds of formula (I) include the following:
N,N'-diphenyl-N,N'-bis(trifluoromethylsulfonyl)oxamide,
N,N'-dinaphthyl-N,N'-bis(trifluoromethylsulfonyl)oxamide,
N,N'-bis(4-chlorophenyl)-N,N'-bis(trifluoromethylsulfonyl)oxamide,
N,N'-bis(2-bromophenyl)-N,N'-bis(trifluoromethylsulfonyl)oxamide,
N,N'-bis(4-fluorophenyl)-N,N'-bis(trifluoromethylsulfonyl)oxamide,
N,N'-bis(3-iodophenyl)-N,N'-bis(trifluoromethylsulfonyl)oxamide,
N,N'-bis(2,4-dichlorophenyl)-N,N'-bis(trifluoromethylsulfonyl)oxamide,
N,N'-bis(2,4-dibromophenyl)-N,N'-bis(trifluoromethylsulfonyl)oxamide,
N,N'-bis(2,5-difluorophenyl)-N,N'-bis(trifluoromethylsulfonyl)oxamide,
N,N'-bis(4-bromo-2-chorophenyl)-N,N'-bis(trifluoromethylsulfonyl)oxamide,
N,N'-bis(2-chloro-4-fluorophenyl)-N,N'-bis(trifluoromethylsulfonyl)oxamide,
N,N'-bis(2,4,5-trichlorophenyl)-N,N'-bis(trifluoromethylsulfonyl)oxamide,
N,N'-bis(2,4,6-trichlorophenyl)-N,N'-bis(trifluoromethylsulfonyl)oxamide,
N,N'-bis(3,4,5-trichlorophenyl)-N,N'-bis(trifluoromethylsulfonyl)oxamide,
N,N'-bis(2,4-dichloro-6-fluorophenyl)-N,N'-bis-(trifluoromethylsulfonyl)oxamide,
N,N'-bis(2,6-dichloro-4-fluorophenyl)-N,N'-bis-(trifluoromethylsulfonyl)oxamide, N,N'-bis(2,3,5,6-tetrachlorophenyl)-N,N'-bis-(trifluoromethylsulfonyl)oxamide,
N,N'-bis(2,3,4,5,6-pentafluorophenyl)-N,N'-bis-(trifluoromethylsulfonyl)oxamide,
N,N'-bis(4-nitrophenyl)-N,N'-bis(trifluoromethylsulfonyl)oxamide,
N,N'-bis(2,4-dinitrophenyl)-N,N'-bis(trifluoromethylsulfonyl)oxamide,
N,N'-bis(4-chloro-2-nitrophenyl)-N,N'-bis(trifluoromethylsulfonyl)oxamide,
N,N'-bis(4-fluoro-3-nitrophenyl)-N,N'-bis(trifluoromethylsulfonyl)oxamide,
N,N'-bis(2,5-dichloro-4-nitrophenyl)-N,N'-bis-(trifluoromethylsulfonyl)oxamide,
N,N'-bis(2,6-dichloro-4-nitrophenyl)-N,N'-bis-(trifluoromethylsulfonyl)oxamide,
N,N'-bis(4-cyanophenyl)-N,N'-bis(trifluoromethylsulfonyl)oxamide,
N,N'-bis(4-hydroxyphenyl)-N,N'-bis(trifluoromethylsulfonyl)oxamide,
N,N'-bis(4-carboxyphenyl)-N,N'-bis(trifluoromethylsulfonyl)oxamide,
N,N'-bis(4-ethoxycarbonylphenyl)-N,N'-bis(trifluoromethylsulfonyl)oxamide,
N,N'-bis(4-ethoxysulfonylphenyl)-N,N'-bis(trifluoromethylsulfonyl)oxamide,
N,N'-bis(4-aminocarbonylphenyl)-N,N'-bis(trifluoromethylsulfonyl)oxamide,
N,N'-bis(3-aminosulfonylphenyl)-N,N'-bis(trifluoromethylsulfonyl)oxamide,
N,N'-bis(2-chloro-5-trifluoromethylphenyl)-N,N'-bis(trifluoromethylsulfonyl)oxamide,
N,N'-bis(2-nitro-4-trifluoromethylphenyl)-N,N'-bis(trifluoromethylsulfonyl)oxamide,
N,N'-bis(4-bromo-2-trifluoromethylphenyl)-N,N'-bis(trifluoromethylsulfonyl)oxamide,
N,N'-bis(2-fluoro-5-trifluoromethylphenyl)-N,N'-bis(trifluoromethylsulfonyl)oxamide,
N,N'-bis(2,6-dinitro-4-trifluoromethylphenyl)-N,N'-bis(trifluoromethylsulfonyl)oxamide,
N,N'-bis(2,6-dichloro-4-trifluoromethylphenyl)-N,N'-bis(trifluoromethylsulfonyl)oxamide,
N,N'-bis[3,5-bis(trifluoromethyl)phenyl]-N,N'-bis(trifluoromethylsulfonyl)oxamide,
N,N'-bis(3-trifluoromethylphenyl)-N,N'-bis(trifluoromethylsulfonyl)oxamide,
N,N'-bis(2-methylphenyl)-N,N'-bis(trifluoromethylsulfonyl)oxamide,
N,N'-bis(2,4-dimethylphenyl)-N,N'-bis(trifluoromethylsulfonyl)oxamide,
N,N'-bis(4-n-hexylphenyl)-N,N'-bis(trifluoromethylsulfonyl)oxamide,
N,N'-bis(4-chloro-2-methylphenyl)-N,N'-bis(trifluoromethylsulfonyl)oxamide,
N,N'-bis(2-bromo-4-methylphenyl)-N,N'-bis(trifluoromethylsulfonyl)oxamide,
N,N'-bis(2-methyl-5-nitrophenyl)-N,N'-bis(trifluoromethylsulfonyl)oxamide,
N,N'-bis(2-methoxyphenyl)-N,N'-bis(trifluoromethylsulfonyl)oxamide,
N,N'-bis(4-n-hexyloxyphenyl)-N,N'-bis(trifluoromethylsulfonyl)oxamide,
N,N'-bis(2,5-dimethoxyphenyl)-N,N'-bis(trifluoromethylsulfonyl)oxamide,
N,N'-bis(5-chloro-2-methoxyphenyl)-N,N'-bis(trifluoromethylsulfonyl)oxamide,
N,N'-bis(4-methoxy-2-nitrophenyl)-N,N'-bis(trifluoromethylsulfonyl)oxamide,
N,N'-bis(5-chloro-2,4-dimethoxyphenyl)-N,N'-bis(trifluoromethylsulfonyl)oxamide,
N,N'-bis(3-formylphenyl)-N,N'-bis(trifluoromethylsulfonyl)oxamide,
N,N'-bis(2-acetylphenyl)-N,N'-bis(trifluoromethylsulfonyl)oxamide,
N,N'-bis(3-n-hexanoylphenyl)-N,N'-bis(trifluoromethylsulfonyl)oxamide,
N,N'-bis(3-bromoacetylphenyl)-N,N'-bis(trifluoromethylsulfonyl)oxamide,
N,N'-bis(5-acetyl-2-methoxyphenyl)-N,N'-bis(trifluoromethylsulfonyl)oxamide,
N,N'-bis[2,4-bis(methylsulfonyl)phenyl]-N,N'bis(trifluoromethylsulfonyl)oxamide,
N,N'-bis(4-acetamidophenyl)-N,N'-bis(trifluoromethylsulfonyl)oxamide,
N,N'-bis(4-benzamidophenyl)-N,N'-bis(trifluoromethylsulfonyl)oxamide,
N,N'-bis(3-propionamidophenyl)-N,N'-bis(trifluoromethylsulfonyl)oxamide,
N,N'-bis(3-acetamido-4-chlorophenyl)-N,N'-bis(trifluoromethylsulfonyl)oxamide,
N,N'-bis(5-acetamido-2-methylphenyl)-N,N'-bis-(trifluoromethylsulfonyl)oxamide,
N,N'-bis(3-acetamido-4-trifluoromethylphenyl)-N,N'-bis(trifluoromethylsulfonyl)oxamide,
N,N'-bis(2-acetamido-4-methoxyphenyl)-N,N'-bis(trifluoromethylsulfonyl)oxamide,
N,N'-bis(5-chloroacetamido-2-methylphenyl)-N,N'-bis(trifluoromethylsulfonyl)oxamide,
N,N'-bis(2-chloro-5-chloroacetamidophenyl)-N,N'-bis(trifluoromethylsulfonyl)oxamide,
N,N'-diethyl-N,N'-bis(trifluoromethylsulfonyl)oxamide,
N,N'-dihydro-N,N'-bis(trifluoromethylsulfonyl)oxamide,
N,N'-di-n-butyl-N,N'-bis(trifluoromethylsulfonyl)oxamide,
N,N'-di-n-propyl-N,N'-bis(trifluoromethylsulfonyl)oxamide,
N,N'-dicyclohexyl-N,N'-bis(trifluoromethylsulfonyl)oxamide,
N,N'-dimethyl-N,N'-bis(trifluoromethylsulfonyl)oxamide,
N,N'-diisopropyl-N,N'-bis(trifluoromethylsulfonyl)oxamide,
N,N'-diacetyl-N,N'-bis(trifluoromethylsulfonyl)oxamide,
N,N'-dihexanoyl-N,N'-bis(trifluoromethylsulfonyl)oxamide,
N,N'-diisobutyroyl-N,N'-bis(trifluoromethylsulfonyl)oxamide,
N,N'-bis(2-chloroethyl)-N,N'-bis(trifluoromethylsulfonyl)oxamide,
N,N'-bis(2-bromoethyl)-N,N'-bis(trifluoromethylsulfonyl)oxamide,
N,N'-bis(2-fluoroethyl)-N,N'-bis(trifluoromethylsulfonyl)oxamide,
N,N'-bis(trifluoromethyl)-N,N'-bis(trifluoromethylsulfonyl)oxamide,
N,N'-bis(3-chloropropyl)-N,N'-bis(trifluoromethylsulfonyl)oxamide,
N,N'-bis(2-n-hexyloxyethyl)-N,N'-bis(trifluoromethylsulfonyl)oxamide,
N,N'-bis(2-nitroethyl)-N,N'-bis(trifluoromethylsulfonyl)oxamide,
N,N'-dibenzyl-N,N'-bis(trifluoromethylsulfonyl)oxamide, N,N'-di-1-phenethyl-N,N'-bis(trifluoromethylsulfonyl)oxamide,
N,N'-di-(1-naphthylmethyl)-N,N'-bis(trifluoromethylsulfonyl)oxamide,
N,N'-bis(2,6-dichlorobenzyl)-N,N'-bis(trifluoromethylsulfonyl)oxamide,
N,N'-bis(2-nitrobenzyl)-N,N'-bis(trifluoromethylsulfonyl)oxamide,
N,N'-bis(4-cyanobenzyl)-N,N'-bis(trifluoromethylsulfonyl)oxamide,
N,N'-bis(4-methylbenzyl)-N,N'-bis(trifluoromethylsulfonyl)oxamide,
N,N'-bis(3-acetylbenzyl)-N,N'-bis(trifluoromethylsulfonyl)oxamide,
N,N'-bis(2-methoxyethyl)-N,N'-bis(trifluoromethylsulfonyl)oxamide,
N,N'-bis(2-morpholylethyl)-N,N'-bis(trifluoromethylsulfonyl)oxamide,
N,N'-bis(2-piperidylethyl)-N,N'-bis(trifluoromethylsulfonyl)oxamide,
N,N'-bis(3-pyridyl)-N,N'-bis(trifluoromethylsulfonyl)oxamide,
N,N'-bis(2-pyridyl)-N,N'-bis(trifluoromethylsulfonyl)oxamide,
N,N'-bis(4-pyridyl)-N,N'-bis(trifluoromethylsulfonyl)oxamide,
N,N'-bis(2-chloro-3-pyridyl)-N,N'-bis(trifluoromethylsulfonyl)oxamide,
N,N'-bis(2-furanyl)-N,N'-bis(trifluoromethylsulfonyl)oxamide,
N,N'-bis(2-thienyl)-N,N'-bis(trifluoromethylsulfonyl)oxamide,
N,N'-bis[2-(2-pyridyl)ethyl]-N,N'-bis(trifluoromethylsulfonyl)oxamide,
N,N'-bis(2-thienyl)-N,N'-bis(trifluoromethylsulfonyl)oxamide,
N,N'-bis(2-furfuryl)-N,N'-bis(trifluoromethylsulfonyl)oxamide,
N,N'-bis(4-methylsulfonylbenzyl)-N,N'-bis(trifluoromethylsulfonyl)oxamide,
N,N'-bis(benzhydryl)-N,N'-bis(trifluoromethylsulfonyl)oxamide,
N,N'-bis(4-methylaminocarbonylphenyl)-N,N'-bis(trifluoromethylsulfonyl)oxamide,
N,N'-bis(4-phenylaminocarbonylphenyl)-N,N'-bis(trifluoromethylsulfonyl)oxamide,
N,N'-bis(4-o-bromophenylaminocarbonylphenyl)-N,N'-bis(trifluoromethylsulfonyl)oxamide,
and the sodium, potassium, lithium, ammonium, methylammonium, n-hexylammonium, diethylammonium, tri-n-butylammonium, and tetraethylammonium salts of
N,N'-bis(4-carboxyphenyl)-N,N'-bis(trifluoromethylsulfonyl)oxamide,
N,N'-bis(2-carboxyphenyl)-N,N'-bis(trifluoromethylsulfonyl)oxamide,
N,N'-bis(4-sulfophenyl)-N,N'-bis(trifluoromethylsulfonyl)oxamide, and
N,N'-bis(2-sulfophenyl)-N,N'-bis(trifluoromethylsulfonyl)oxamide,
and the like.

The preferred compounds are as follows:
N,N'-bis(2,4-dichlorophenyl)-N,N'-bis(trifluoromethylsulfonyl)oxamide,
N,N'-bis(2,4,5-trichlorophenyl)-N,N'-bis(trifluoromethylsulfonyl)oxamide,
N,N'-bis(2,4,6-trichlorophenyl)-N,N'-bis(trifluoromethylsulfonyl)oxamide,
N,N'-bis(4-nitrophenyl)-N,N'-bis(trifluoromethylsulfonyl)oxamide,
N,N'-bis(2-methoxyethyl)-N,N'-bis(trifluoromethylsulfonyl)oxamide,
N,N'-bis(4-chlorophenyl)-N,N'-bis(trifluoromethylsulfonyl)oxamide,
N,N'-bis(2-chloro-3-pyridyl)-N,N'-bis(trifluoromethylsulfonyl)oxamide, The particularly preferred compound is N,N'-bis(2,4,5-trichlorophenyl)-N,N'-bis(trifluoromethylsulfonyl)oxamide.

The term "chemiluminescence," as employed herein, is defined as the generation of electromagnetic radiation between about 300 and 1200 nanometers by means of a chemical reaction.

The term "composition for reaction with a peroxide component to generate chemiluminescence," as employed herein, is defined as a mixture of a compound of formula (I) and a fluorescer compound in a diluent in concentrations sufficient to produce chemiluminescence when combined with a peroxide component. Thus, the initial concentrations of the compound of formula (I), fluorescer compound, and the ingredients of the peroxide component in the reaction mixture must be sufficient to produce chemiluminescence.

The fluorescer compounds contemplated herein may be broadly defined as those which do not readily react with the peroxide component employed in this invention or with the compound of formula (I).

Typical suitable fluorescent compounds for use in the present invention are those which have a spectral emission falling between 300 and 1200 nanometers and which are at least partially soluble in the diluent employed. Among these are the conjugated polycyclic aromatic compounds having at least 3 fused rings, such as: anthracene, substituted anthracene, benzanthracene, phenanthrene, substituted phenanthrene, naphthacene, substituted naphthacene, pentacene, substituted pentacene, perylene, substituted perylene, violanthrone, substituted violanthrone, and the like. Typical substituents for all of these are phenyl, lower alkyl, chlorine, bromine, cyano, alkoxy ($C_1$–$C_{16}$), and other like substituents which do not interfere with the light-generating reaction contemplated herein.

Numerous other fluorescent compounds having the properties given hereinabove are well-known in the art. Many of these are fully described in "Fluorescence and Phosphorescence," by Peter Pringsheim, Interscience Publishers, Inc., New York, N.Y., 1969. Other fluorescers are described in "The Colour Index," Second Edition, Volume 2, The American Association of Textile Chemists and Colorists, 1956, pp. 2907–2923. While only typical fluorescent compounds are listed hereinabove, the person skilled in the art is fully aware of the fact that this invention is not so restricted, and that numerous other fluorescent compounds having similar properties are contemplated for use herein.

The preferred fluorescer compound is a 9,10-bis(phenylethynyl)anthracene, as disclosed in U.S. Pat. No. 3,888,786, which is incorporated herein by reference.

The 9,10-bis(phenylethynyl)anthracene compounds contemplated herein may be defined as 9,10-bis(phenylethynyl)anthracene, or chloro, bromo, fluoro, or lower alkyl-substituted bis(phenylethynyl)anthracenes. The preferred compound is selected from 9,10-bis(phenylethynyl)anthracene or chlorosubstituted 9,10-bis(phenylethynyl)anthracenes. More preferably, the compound is selected from 9,10-bis(phenylethynyl)anthracene, 1-chloro-9,10-bis(phenylethynyl)anthracene, or 2-chloro-9,10-bis(phenylethynyl)anthracene.

Illustrative of the 9,10-bis(phenylethynyl)anthracenes which can be used in this invention are the following:
9,10-bis(phenylethynyl)anthracene,
1-chloro-9,10-bis(phenylethynyl)anthracene,
2-chloro-9,10-bis(phenylethynyl)anthracene,
1,5-dichloro-9,10-bis(phenylethynyl)anthracene,
1,8-dichloro-9,10-bis(phenylethynyl)anthracene,
1-bromo-9,10-bis(phenylethynyl)anthracene,
1-fluoro-9,10-bis(phenylethynyl)anthracene,
1-methyl-9,10-bis(phenylethynyl)anthracene,
and the like.

The term "diluent," as used herein, is defined as a solvent, or vehicle, which does not cause insolubility of the compound of formula (I), or any of the ingredients of the peroxide component, and in which the fluorescer compound is at least partially soluble.

The term "peroxide component," as used herein, means a solution of a hydrogen peroxide compound, a hydroperoxide compound, or a peroxide compound in a suitable diluent.

The term "hydrogen peroxide compound" includes (1) hydrogen peroxide and (2) hydrogen peroxide-producing compounds.

The composition for reaction with a peroxide component to generate chemiluminescence can contain any fluid diluent which solubilizes the compound of formula (I) and the fluorescer compound to provide initial concentrations in the reacting system of about $10^{-3}$ M to about 10 M, preferably about $10^{-2}$ M to about 1 M, of the compound of formula (I), and about $10^{-5}$ M to about $10^{-1}$ M, preferably about $10^{-4}$ M to $10^{-2}$ M, of the fluorescer compound. The diluent must be relatively unreactive toward the compound of formula (I), the fluorescer compound, and the ingredients of the peroxide component.

The concentrations of the compound of formula (I) and the fluorescer compound in the composition for reaction with the peroxide component is about 1.1–2.5, preferably about 1.2–1.3, times the concentrations of the same materials in the reacting system described above. Typical diluents, or solvents, which can be used include esters, ethers, aromatic hydrocarbons, chlorinated aliphatic and aromatic hydrocarbons such as those disclosed in U.S. Pat. No. 3,749,679. The preferred diluent is dibutyl phthalate. Solvent combinations may, of course, be used but such combinations should not include strongly electron donating solvents.

Hydrogen peroxide is the preferred hydroperoxide and may be employed as a solution of hydrogen peroxide in a solvent or as an anhydrous hydrogen peroxide compound such as sodium perborate, sodium peroxide, and the like. Whenever hydrogen peroxide is contemplated to be employed, any suitable compound may be substituted which will produce hydrogen peroxide.

Diluents which can be employed in the peroxide component include any fluid which is relatively unreactive toward the hydroperoxide, the compound of formula (I) and the fluorescer compound, and which accommodates a solubility to provide at least 0.01 M hydroperoxide. Typical solvents for the hydroperoxide component include water; alcohols, such as ethanol, tertiary butanol, or octanol; ethers, such as diethyl ether, diamly ether, tetrahydrofuran, dioxane, dibutyldiethyleneglycol, perfluoropropyl ether, and 1,2-dimethoxyethane; and esters, such as ethyl acetate, ethyl benzoate, dimethyl phthalate, dioctylphthalate, propyl formate. Solvent combinations can, of course, be used such as combinations of the above with anisole, tetralin, and chlorobenzene, providing said solvent combination accomodates hydroperoxide solubility. However, strong electron donor solvents such as dimethyl formamide, dimethyl sulfoxide, and hexamethylphosphoramide should not, in general, be used as a major diluent for the peroxide component.

The preferred diluent for the peroxide component is a mixture of about 80 volume percent dimethyl phthalate and about 20 volume percent tertiary butanol.

The hydrogen peroxide concentration in the peroxide component may range from about 0.2 M to about 15 M. Preferably, the concentration ranges from about 1 M to about 2 M.

The lifetime and intensity of the chemiluminescent light emitted can be regulated by the use of certain regulators such as:

(1) By the addition of a catalyst which changes the rate of reaction of hydroperoxide with the compound of formula (I). Catalysts which accomplish that objective include those described in M. L. Bender, "Chem. Revs.," Vol. 60, p. 53 (1960). Also, catalysts which alter the rate of reaction or the rate of chemiluminescence include those accelerators of U.S. Pat. No. 3,775,366, and decelerators of U.S. Pat. Nos. 3,691,085 and 3,704,231, or (2) By the variation of hydroperoxide. Both the type and the concentration of hydroperoxide are critical for the purposes of regulation.

Preferably, a weakly basic accelerator, such as sodium salicylate, is included in the peroxide component to control the lifetime of the chemical lighting system. The concentration of weakly basic accelerator used in the peroxide component may range from about $10^{-6}$ M to about $10^{-2}$ M, preferably from about $10^{-4}$ M to about $10^{-3}$ M.

The initial concentration of the ingredients of the peroxide component in the reacting system is about 0.15 to 0.60 of the concentrations in the peroxide component since the peroxide component comprises about 15 to about 60 volume percent of the reaction mixture.

The concentration of the hydrogen peroxide compound in the chemiluminescent reaction is at least equal to the molar concentration of the compound of formula (I) and is preferably 1.2 to 5.0 times the concentration of the compound of formula (I) in the reacting system described above. The optimum concentrations must be determined experimentally for each specific system.

The following examples are illustrative of the present invention. All parts are by weight unless otherwise indicated.

EXAMPLE 1

Preparation of
N-2,4,5-Trichlorophenyl-Trifluoromethanesulfonamide

Trifluoromethanesulfonic anhydride (14.11 grams; 0.05 mole) is added in portions to a stirred solution of 2,4,5-trichloroaniline (9.8 grams; 0.05 mole) and triethylamine (5.0 grams; 0.05 mole) in methylene chloride (50 mls) at 0° C. under a nitrogen atmosphere. The reaction mixture is stirred at 0° C. for one hour upon completion of the addition, then heated to 50° C. and stirred thereat for 3 hours. The white solid precipitate is separated by filtration and the filtrate is evaporated to obtain a dark oil. Water (40 mls) is added to the oil and the resulting mixture is extracted three times with diethyl ether (50 mls). The combined ethereal extracts are then dried over anhydrous sodium sulfate, the dried extract is separated and the separated ethereal solution is evaporated to obtain 13.4 grams of crude product. Recrystallization of the crude product from methylcyclohexane gives the desired product, m.p. 104°–106° C.

Analysis-Calculated for $C_7H_3Cl_3F_3NO_2S$ (percent): C,25.69; H,0.92; Cl,32.11; F,17.43; N,4.28; S,9.79. Found (percent): C,25.59; H,1.00; Cl,31.98; F,17.00; N,4.35; S,9.95.

In the manner described above and in U.S. Pat. No. 3,799,968, using the appropriately substituted anilines, and amines, the following compounds are prepared:
N-phenyltrifluoromethanesulfonamide,
N-(4-chlorophenyl)trifluoromethanesulfonamide,
N-(2,4-dichlorophenyl)trifluoromethanesulfonamide,
N-(2,4,5-trichlorophenyl)trifluoromethanesulfonamide,
N-(2,4,6-trichlorophenyl)trifluoromethanesulfonamide,
N-(4-nitrophenyl)trifluoromethanesulfonamide,
N-(2-methoxyethyl)trifluoromethanesulfonamide,
N-methyltrifluoromethanesulfonamide,
N-(2-bromoethyl)trifluoromethanesulfonamide,
N-(2-chloro-3-pyridyl)trifluoromethanesulfonamide,
N-(2-chloroethyl)trifluoromethanesulfonamide,
N-(2-morpholylethyl)trifluoromethanesulfonamide, and
N-(2-piperidylethyl)trifluoromethanesulfonamide.

EXAMPLE 2

Preparation of
N,N'-Bis(2,4-dichlorophenyl)-N,N'-Bis(trifluoromethylsulfonyl)Oxamide Oxalyl chloride (1.90 grams; 0.015 mole) is added dropwise to a solution of N-2,4-dichlorophenyltrifluoromethanesulfonamide (5.94 grams; 0.02 mole) and triethylamine (2.0 grams; 0.02 mole) in 1,2-dimethoxyethane (50 mls) at 0° C. under a nitrogen atmosphere. After the addition is completed, the reaction mixture is heated to 70° C. and held thereat for 5 hours. The reaction mixture is filtered to remove insolubles and the filtrate is evaporated to obtain 6.05 grams (94% of theoretical) of crude product.

Recrystallization of the crude product from cyclohexane affords the desired product, m.p. 148°–150° C.

Calculated for $C_{16}H_6N_2O_6Cl_4F_6S_2$: C,29.95%; H,0.90%; N,4.36%; Cl,22.12%; F,17.75%; S,10.00%. Found: C,30.24%; H,1.02%; N,4.24%; Cl,22.27%; F,17.19%; S,10.45%.

EXAMPLE 3

Preparation of
N,N'-Bis(2,4,5-trichlorophenyl)-N,N'-Bis(trifluoromethylsulfonyl)Oxamide Method A:

Oxalyl chloride (1.27 grams; 0.01 mole) is added portionwise to a stirred solution of N-2,4,5-trichlorophenyl trifluoromethanesulfonamide (6.2 grams; 0.02 mole) and triethylamine (2.0 grams; 0.02 mole) in methylene chloride (50 mls) at 0° C. under a nitrogen atmosphere. After the addition is completed, the reaction mixture is stirred at room temperature for 4 hours and then filtered to obtain 2.1 grams of crude product.

Recrystallization of the crude product from methylcyclohexane affords the desired product, m.p. 190°–192° C.

Calculated for $C_{16}H_4N_2O_6Cl_6F_6S_2$: C,27.02%; H,0.57%; N,3.94%; Cl,29.91%; F,16.04%, S,9.02%. Found: C,27.02%; H,0.63%; N,3.84%; Cl,30.06%; F,16.64%; S,8.90%.

Evaporation of the filtrate, obtained by isolating the crude product and triturating the residue with water, gives an additional 3.5 grams of crude product after filtering and drying. The total yield in two crops is 78.7% of theoretical.

Method B:

Oxalyl chloride (4.44 grams; 0.035 mole) is added in portions to a suspension of N-2,4,5-trichlorophenyl trifluoromethylsulfonamide (15.0 grams; 0.06 mole) and powdered molecular sieves (15 grams; Molecular Sieve, Type 3A from Union Carbide Corporation) in methylene chloride (150 mls) at 0° C. under a nitrogen atmosphere. After the addition is completed, the reaction mixture is heated to 60° C. and stirred thereat for 5 hours. The molecular sieves are then separated by filtration and the filtrate is concentrated to remove the methylene chloride and obtain 17.45 grams (82% of theoretical) of crude product.

Recrystallization of the crude product from methylcyclohexane gives a product identical with that obtained by Method A.

EXAMPLE 4

Preparation of
N,N'-Bis(4-nitrophenyl)-N,N'-Bis(trifluoromethylsulfonyl)Oxamide

Oxalyl chloride (0.825 gram; 0.0065 mole) is added dropwise to a stirred solution of N-4-nitrophenyl trifluoromethanesulfonamide (3.61 grams; 0.013 mole) and triethylamine (1.3 grams; 0.0128 mole) in dry tetrahydrofuran (40 mls) at 0° C. under a nitrogen atmosphere. After the addition is completed, the reaction mixture is warmed to room temperature and stirred thereat for 18 hours. The reaction mixture is then filtered, the solvent is evaporated from the filtrate, and water (20 mls) is added to the residue. The resulting precipitate is then filtered to obtain 3.29 grams (92% of theoretical) of crude yellow-colored product.

Recrystallization of the crude product from diethyl ether gives the desired product, m.p. 172°–175° C.

Calculated for $C_{16}H_8N_4O_{10}F_6S_2$: C,34.16%; H,1.42%; N,9.96%; F,20.28%; S,11.39%. Found: C,34.46%; H,1.25%; N,9.80%; F,19.82%; S,11.78%.

EXAMPLE 5

Preparation of
N,N'-Bis(2-methoxyethyl)-N,N'-Bis(trifluoromethylsulfonyl)Oxamide Oxalyl chloride (1.27 grams; 0.01 mole) is added portionwise to a stirred solution of N-(2-methoxyethyl)trifluoromethanesulfonamide (4.0 grams; 0.02 mole) and triethylamine (2.0 grams; 0.02 mole) in 1,2-dimethoxyethane (40 mls) at 0° C. under a nitrogen atmosphere. After the addition is completed, the reaction mixture is stirred at 0° C. for one hour, heated to 50° C. and stirred thereat for 2 hours, and concentrated to remove the solvent. The residue is then extracted with diethyl ether and the ether extract is evaporated to obtain 4.65 grams (99% of theoretical) of crude product.

Vacuum distillation of the crude product gives the pure product, b.p. 74°–76° C. at 0.5 mm.

Calculated for $C_{10}H_{14}N_2O_8F_6S_2$: C,25.64%, H,2.99%; N,5.98%; F,24.36%; S,13.68%. Found: C,25.60%; H,3.11%; N,5.77%; F,23.95%; S,13.92%.

EXAMPLE 6

Preparation of N,N'-Bis(4-chlorophenyl)-N,N'-Bis(trifluoromethylsulfonyl)Oxamide Oxalyl chloride (0.635 gram; 0.005 mole) is added dropwise to a stirred solution of N-4-chlorophenyl-trifluoromethanesulfonamide (2.6 grams; 0.01 mole) and triethylamine (1.0 gram; 0.01 mole) in 1,2-dimethoxyethane (20 mls) at 0° C. under a nitrogen atmosphere. The mixture is stirred at 0° C. for 2 hours, heated to 60° C. and held at 60° C. for one hour, and evaporated to obtain a yellow solid which is then treated with 20 mls of water.

Recrystallization of the remaining solid from anhydrous ether gave 2.46 grams of the desired product as white crystals which melted at 173°–174° C. The yield is 85.8% of theoretical.

Calculated for $C_{16}H_8N_2Cl_2S_2O_6F_6$: C,33.50%; H,1.40%; N,4.88%; Cl,12.40%; S,11.17%; F,19.90%. Found: C,33.51%; H,1.38%; N,4.74%; Cl,12.10%; S,11.52%; F,19.11%.

EXAMPLE 7

Preparation of N,N'-Bis(2-chloro-3-pyridyl)-N,N'-Bis(trifluoromethylsulfonyl)Oxamide Oxalyl chloride (0.762 gram; 0.006 mole) is added dropwise to a suspension of N-(2-chloro-3-pyridyl)trifluoromethanesulfonamide (2.61 grams; 0.01 mole) and powdered molecular sieves (5.0 grams; Molecular Sieve, Type 3A) in methylene chloride (75 mls) at 0° C. under a nitrogen atmosphere. The mixture is then heated to 60° C., held thereat for 3 hours, and then stirred at room temperature for 60 hours. The reaction mixture is filtered and the filtrate is evaporated to dryness. The resulting residue is extracted with diethyl ether, and the combined ethereal extracts are dried over anhydrous sodium sulfate. The dried ethereal extract is then separated and evaporated to obtain 2.33 grams (81% of theoretical) of crude product.

Recrystallization of the crude product from cyclohexane gives the desired product, m.p. 104°–106° C.

Calculated for $C_{14}H_6N_4O_6Cl_2F_6S_2$: C,29.27%; H,1.05%; N,9.76%; Cl,12.20%; F,19.86%; S,11.15%. Found: C,29.10%; H,1.14%; N,9.51%; Cl,11.95% F,19.40%; S,10.89%.

In the manner described above using 0.01 mole of the appropriately substituted trifluoromethanesulfonamide, the following compounds are prepared:

N,N'-bis(trifluoromethylsulfonyl)oxamide,
N,N'-bis(di-n-butyl)-N,N'-bis(trifluoromethylsulfonyl)oxamide,
N,N'-dihexanoyl-N,N'-bis(trifluoromethylsulfonyl)oxamide,
N,N'-bis(2-bromoethyl)-N,N'-bis(trifluoromethylsulfonyl)oxamide,
N,N'-bis(2-chloroethyl)-N,N'-bis(trifluoromethylsulfonyl)oxamide,
N,N'-bis(2-n-hexyloxy)-N,N'-bis(trifluoromethylsulfonyl)oxamide,
N,N'-bis(dibenzyl)-N,N'-bis(trifluoromethylsulfonyl)oxamide,
N,N'-bis(2,6-dichlorobenzyl)-N,N'-bis(trifluoromethylsulfonyl)oxamide,
N,N'-bis[2-(2-pyridyl)ethyl]-D,N'-bis(trifluoromethylsulfonyl)oxamide,
N,N'-bis(2-furfanyl)-N,N'-bis(trifluoromethylsulfonyl)oxamide,
N,N'-bis(2-thienyl)-N,N'-bis(trifluoromethylsulfonyl)oxamide,
N,N'-bis(4-aminocarbonylphenyl)-N,N'-bis(trifluoromethylsulfonyl)oxamide,
N,N'-bis(2-morpholylethyl)-N,N'-bis(trifluoromethylsulfonyl)oxamide, and
N,N'-bis(2-piperidylethyl)-N,N'-bis(trifluoromethylsulfonyl)oxamide.

EXAMPLE 8

Determination of Chemiluminescence

A solution (7.5 mls) of 1-chloro-9,10-bis(phenylethynyl)anthracene (CBPEA) and the reactant under study, in dibutyl phthalate, is mixed with 2.5 mls of peroxide component comprising hydrogen peroxide and sodium salicylate in 80% dimethyl phthalate—20% tertiary butanol, by volume, to provide a reaction mixture having initial concentrations of 0.38 M hydrogen peroxide, $0.3 \times 10^{-3}$ M sodium salicylate, $6.75 \times 10^{-3}$ M CBPEA, and the concentration of reactant indicated in Table I, and quantitative measurements of the chemiluminescence of the different systems are carried out by measuring the intensity of the light emitted at 555 nanometers by means of a Hirt-Roberts radiometer-spectrophotometer. The results obtained are summarized in Table I.

TABLE I

| Reactant | Conc. (Molar) | Light Capacity[a] | Quantum Yield[b] |
|---|---|---|---|
| Compound of Example 3 | 0.01 | 112.50 | 34.00 |
| Compound of Example 6 | 0.01 | 37.47 | 11.44 |
| Compound of Example 4 | 0.01 | 35.70 | 11.00 |
| Compound of Example 2 | 0.1 | 69.89 | 21.40 |
| Compound of Example 5 | 0.1 | 9.20 | 2.85 |
| Compound of Example 7 | 0.008 | 41.30 | 15.50 |

[a]Lumen hours per liter of emitting solution
[b]Einsteins per mole $\times 10^2$

We claim:

1. A compound represented by formula (I)

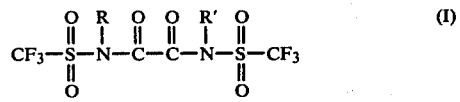

wherein R and R' independently represent hydrogen; alkyl of 1 to 6 carbon atoms; cycloalkyl of 4 to 8 carbon atoms; substituted alkyl or cycloalkyl wherein the substituents are selected from halo, carboxy, alkoxy, or alkoxycarbonyl, wherein the alkoxy is of 1 to 6 carbon atoms; alkanoyl of 2 to 18 carbon atoms; aroyl of 7 to 11 carbon atoms; aralkyl of 7 to 11 carbon atoms; aryl of 6 to 10 carbon atoms; heterocyclic aryl of 3 to 9 carbon atoms; substituted aryl and heterocyclic aryl of 6 to 10 and 3 to 9 carbon atoms, respectively, wherein the substituents, one or more, are selected from halo, nitro, cyano, trifluoromethyl, alkyl and alkoxy of 1 to 6 carbon atoms, hydroxy, phenoxy, benzyloxy, phenyl, alkanoylamino of 2 to 6 carbon atoms, benzoylamino, alkylsulfonyl of 1 to 6 carbon atoms, carboxy, alkoxycarbonyl and alkoxysulfonyl wherein the alkoxy group has 1 to 6 carbon atoms, $-SO_3^{\ominus}M^{\oplus}$ wherein $M^{\oplus}$ is a cation selected from sodium, potassium, lithium, ammonium, monoalkylammonium, dialkylammonium, trialkylammonium, or tetraalkylammonium wherein the alkyl radicals have 1 to 6 carbon atoms, and may be the same or different, aminocarbonyl, and aminosulfonyl which are unsubstituted or substituted at the nitrogen by 1 or 2 radicals selected from alkyl of 1 to 6 carbon atoms, phenyl, or substituted phenyl wherein the substituents are as defined above for aryl and heterocyclic aryl.

2. The compound of claim 1 wherein R and R' are 4-chlorophenyl.

3. The compound of claim 1 wherein R and R' are 2,4-dichlorophenyl.

4. The compound of claim 1 wherein R and R' are 2,4-5-trichlorophenyl.

5. The compound of claim 1 wherein R and R' are 2,4-6-trichlorophenyl.

6. The compound of claim 1 wherein R and R' are 4-nitrophenyl.

7. The compound of claim 1 wherein R and R' are 2-methoxyethyl.

8. The compound of claim 1 wherein R and R' are 2-chloro-3-pyridyl.

9. The compound of claim 1 wherein R and R' are 2-chloroethyl.

10. A composition for reaction with a peroxide component to generate chemiluminescence comprising a mixture of a member selected from the group consisting of N,N'-bis(trifluoromethylsulfonyl)oxamide and N,N'-disubstituted derivatives thereof, with an organic fluorescer dissolved in a liquid diluent for said mixture, in proportions to produce chemiluminescence by said reaction with a peroxide component.

11. The composition of claim 10 wherein said selected member is N,N'-bis(4-chlorophenyl)-N,N'-bis(trifluoromethylsulfonyl)oxamide.

12. The composition of claim 10 wherein said selected member is N,N'-bis(2,4-dichlorophenyl)-N,N'-bis(trifluoromethylsulfonyl)oxamide.

13. The composition of claim 10 wherein said selected member is N,N'-bis(2,4,5-trichlorophenyl)-T,N'-bis(trifluoromethylsulfonyl)oxamide.

14. The composition of claim 10 wherein said selected member is N,N'-bis(2,4,6-trichlorophenyl)-N,N'-bis(trifluoromethylsulfonyl)oxamide.

15. The composition of claim 10 wherein said selected member is N,N'-bis(4-nitrophenyl)-N,N'-bis(trifluoromethylsulfonyl)oxamide.

16. The composition of claim 10 wherein said selected member is N,N'-bis(2-methoxyethyl)-N,N'-bis(trifluoromethylsulfonyl)oxamide.

17. The composition of claim 10 wherein said selected member is N,N'-bis(2-chloro-3-pyridyl)-N,N'-bis(trifluoromethylsulfonyl)oxamide.

18. A process for generating chemiluminescence comprising reacting a peroxide component with the composition of claim 10.

19. A process for generating chemiluminescence comprising reacting hydrogen peroxide with the composition of claim 10.

* * * * *

UNITED STATES PATENT AND TRADEMARK OFFICE
CERTIFICATE OF CORRECTION

PATENT NO. : 4,226,738

DATED : October 7, 1980

INVENTOR(S) : Michael M. Rauhut, Shin-Shyong Tseng and Arthur C. Mohan

It is certified that error appears in the above-identified patent and that said Letters Patent is hereby corrected as shown below:

In Column 1, insert the following statement as the first paragraph of the Specification:

--The invention was made under U.S. Government Contract No. N00014-77-C-0634 and is subject to the provision of ASPR 7-104.18, December, 1969 and ASPR 7.302.23(b) long form August, 1977.--

Signed and Sealed this

Sixth Day of November, 1990

*Attest:*

HARRY F. MANBECK, JR.

*Attesting Officer*  *Commissioner of Patents and Trademarks*